(12) United States Patent
Rubinsky et al.

(10) Patent No.: US 11,130,277 B2
(45) Date of Patent: Sep. 28, 2021

(54) SYSTEMS, APPARATUS AND METHODS FOR CRYOGENIC 3D PRINTING

(71) Applicant: THE REGENTS OF THE UNIVERSITY OF CALIFORNIA, Oakland, CA (US)

(72) Inventors: Boris Rubinsky, El Cerrito, CA (US); Michal Adamkievicz, Lomianki (PL); Ze'Ev Shaked, San Antonio, TX (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 621 days.

(21) Appl. No.: 15/950,106

(22) Filed: Apr. 10, 2018

(65) Prior Publication Data

US 2018/0304537 A1 Oct. 25, 2018

Related U.S. Application Data

(63) Continuation of application No. PCT/US2016/057248, filed on Oct. 15, 2016.
(Continued)

(51) Int. Cl.
*B29C 64/118* (2017.01)
*B33Y 10/00* (2015.01)
(Continued)

(52) U.S. Cl.
CPC .......... *B29C 64/118* (2017.08); *B29C 64/209* (2017.08); *B29C 64/25* (2017.08);
(Continued)

(58) Field of Classification Search
CPC .................................................. B29C 64/364
See application file for complete search history.

(56) References Cited

U.S. PATENT DOCUMENTS

| 5,095,747 A | 3/1992 | Smith |
| 6,253,116 B1 | 6/2001 | Zhang et al. |

(Continued)

FOREIGN PATENT DOCUMENTS

| CN | 103057123 A | 4/2013 |
| CN | 103980681 A | 8/2014 |

(Continued)

OTHER PUBLICATIONS

ISA/US, United States Patent and Trademark Office (USPTO), International Search Report and Written Opinion dated Jan. 17, 2017, related PCT international application No. PCT/US2016/057248, pp. 1-14, claims searched, pp. 15-22.
(Continued)

*Primary Examiner* — Jacob T Minskey
*Assistant Examiner* — Virak Nguon
(74) *Attorney, Agent, or Firm* — O'Banion & Ritchey LLP; John P. O'Banion

(57) ABSTRACT

Systems, apparatus and methods for producing objects with cryogenic 3D printing with controllable micro and macrostructure with potential applications in tissue engineering, drug delivery, and the food industry. The technology can produce complex structures with controlled morphology when the printed 3D object is immersed in a liquid coolant, whose upper surface is maintained at the same level as the highest deposited layer of the object. This ensures that the computer-controlled process of freezing is controlled precisely and already printed frozen layers remain at a constant temperature. The technology controls the temperature, flow rate and volume of the printed fluid emitted by the dispenser that has X-Y positional translation and conditions at the interface between the dispenser and coolant surface. The technology can also control the temperature of the pool of
(Continued)

liquid coolant and the vertical position of the printing surface and pool of coolant liquid.

7 Claims, 3 Drawing Sheets

Related U.S. Application Data

(60) Provisional application No. 62/241,815, filed on Oct. 15, 2015.

(51) Int. Cl.
| | | |
|---|---|---|
| *B33Y 50/02* | (2015.01) | |
| *B29C 64/364* | (2017.01) | |
| *B33Y 40/00* | (2020.01) | |
| *B33Y 70/00* | (2020.01) | |
| *B29C 64/393* | (2017.01) | |
| *B29C 64/371* | (2017.01) | |
| *C12N 5/00* | (2006.01) | |
| *B33Y 30/00* | (2015.01) | |
| *B29C 64/379* | (2017.01) | |
| *B29C 64/209* | (2017.01) | |
| *B29C 64/25* | (2017.01) | |
| *C12M 3/00* | (2006.01) | |

(52) U.S. Cl.
CPC .......... *B29C 64/364* (2017.08); *B29C 64/371* (2017.08); *B29C 64/379* (2017.08); *B29C 64/393* (2017.08); *B33Y 10/00* (2014.12); *B33Y 30/00* (2014.12); *B33Y 40/00* (2014.12); *B33Y 50/02* (2014.12); *B33Y 70/00* (2014.12); *C12M 21/08* (2013.01); *C12N 5/0062* (2013.01); *B29K 2005/00* (2013.01); *B29K 2089/00* (2013.01); *C12N 2513/00* (2013.01)

(56) References Cited

U.S. PATENT DOCUMENTS

| | | | |
|---|---|---|---|
| 8,703,216 B2 | 4/2014 | Forgacs et al. | |
| 8,728,499 B2 | 5/2014 | Zawko et al. | |
| 2008/0145639 A1* | 6/2008 | Sun | B29C 64/118 |
| | | | 428/304.4 |
| 2010/0167020 A1* | 7/2010 | Jones | C04B 38/00 |
| | | | 428/195.1 |
| 2010/0291176 A1* | 11/2010 | Chian | B33Y 10/00 |
| | | | 424/423 |
| 2013/0241114 A1 | 9/2013 | Ravich | |
| 2014/0193456 A1 | 7/2014 | Dyanov | |

FOREIGN PATENT DOCUMENTS

| | | | |
|---|---|---|---|
| KR | 101541249 B1 * | 8/2015 | |
| WO | 2007107571 A2 | 9/2007 | |
| WO | 2015017421 A2 | 2/2015 | |

OTHER PUBLICATIONS

Adamkewicz, Michal et al., "Cryogenic 3D printing for tissue engineering", Cryobiology, 71(3), 518-521, Dec. 2015, http://dx.doi.org/10.1016/j.cryobiol.2015.10.152, retrieved from https://escholarship.org/uc/item/7533g6sj, published online Nov. 5, 2015.

Kim, GeunHyung et al., "A cryogenic direct-plotting system for fabrication of 3D collagen scaffolds for tissue engineering", J. Mater. Chem., 2009, 19, 8817-8823, published online Oct. 12, 2009.

European Patent Office (EPO), "Communication pursuant to Article 94(3) EPC" (official action) dated Apr. 1, 2020, related European patent application No. 16856378.1, pp. 1-4, claims examined, pp. 5-9.

European Patent Office (EPO), supplementary European search report dated Jun. 3, 2019, related European patent application No. 16856378.1, pp. 1-8, claims searched, pp. 9-14.

* cited by examiner

SYSTEMS, APPARATUS AND METHODS FOR CRYOGENIC 3D PRINTING

CROSS-REFERENCE TO RELATED APPLICATIONS

This application is a 35 U.S.C. § 111(a) continuation of PCT international application number PCT/US2016/057248 filed on Oct. 15, 2016, incorporated herein by reference in its entirety, which claims priority to, and the benefit of, U.S. provisional patent application Ser. No. 62/241,815 filed on Oct. 15, 2015, incorporated herein by reference in its entirety. Priority is claimed to each of the foregoing applications.

The above-referenced PCT international application was published as PCT International Publication No. WO 2017/066727 on Apr. 20, 2017, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND

1. Technical Field

The present technology pertains generally to additive manufacturing devices and manufacturing methods for producing three dimensional objects, and more particularly to systems, apparatus and methods for producing freeze-dried or frozen material structures using 3D printing.

2. Background Discussion

Rapid prototyping technologies have been developed as an alternative to conventional milling techniques to produce prototypes of mechanical components, device housings, models and other complex three-dimensional structures. Unlike milling, that removes material to produce an object, additive layer manufacturing (ALM) builds a solid object from the application of successive layers of material printed and formed on top of the previous layer. The application of layers is typically laid down via computer control over the deposition of material.

ALM techniques generally use one of two different printing approaches: 1) laser or electron beams that cure or sinter material in each layer, or 2) ejection of a binder material from a nozzle head to create a patterned layer. The powder materials are fused together at any location where the laser or ejected material comes in contact with the surface of the powder. Many different types of materials can be used to form the patterned layers depending on the process that is used to form the product including, photopolymers, thermopolymers, plastics and metal powders.

One common technological element with current ALM techniques is that the material used in each layer undergoes a phase transformation from a malleable state of matter when it is added to the object to a solid state of matter. This phase transformation, which occurs on the last additive layer, is responsible for incorporating the new layer into the previous layer to form the manufactured object.

For example, one conventional 3D printing technology employs a printer head that delivers the material to be printed, in a molten form, at a controlled rate and temperature. The head has the ability to move in the X-Y plane and the printing table can move on the Z-axis under computer control enabling the manufacturing of complex shapes. The molten material is deposited on the printing table where it solidifies. The process continues until a layer is completed, then the printing table moves downwards and another layer is deposited. This process usually occurs in open air and room temperature, and the phase transition temperature of the molten plastic is higher than room temperature.

However, there are situations where it is desirable for the printed object to have a phase transition temperature that is lower than room temperature. For example, patterned frozen materials or patterned materials that have been "freeze dried" can have useful applications and produce structures that are not available with current technology. Three-dimensional printing technology with precise control over the microstructure of the product would have many applications in life sciences, such as in the field of tissue engineering where the freeze-drying process is critical to generating and maintaining temperature-sensitive complex biological materials. Tissue engineering is a specialized field of life sciences and biomedical engineering established to address failing human organs and tissues by replacing them with functional artificial organs. In addition, applications in the form of micro-organs or organs on a chip have emerged as replacement for the use of animals in research. New approaches and tools are needed to enable practical solutions in tissue engineering.

Generally, there are two elements in the manufacturing of an engineered tissue, namely, the deposition of an extracellular matrix and the printing of cells. One necessary element and requirement of tissue engineering is the ability to manufacture complex tissue scaffolds that can act as an extracellular matrix. Various materials and methods have been attempted for generating a tissue scaffold. Conventional printing materials such as thermoplastics, polymers or metal powders are not biocompatible and therefore not suitable for scaffold production. Nevertheless, 3D additive methods are of increasing interest in tissue engineering in general, and are becoming an enabling tool to design and generate scaffolds.

Another issue with cell printing is that the printing process is time consuming, and often the printed cells die when a large scaffold structure is required. This is why additive methods have been suggested primarily for the production of micro-organs or organs on a chip.

Present approaches to the formation of printed structures that are frozen usually involve either the deposition of very small droplets onto a cooled surface, or releasing very small droplets to fall through a cooling liquid onto a surface. Rapid freezing of biological matter in a liquid cryogen has been known for almost a century and is actually the first method by which cells were preserved at cryogenic temperatures, through vitrification. Cryopreservation using droplets which contain cells and fall into a cryogen is a well-established method.

One type of printing method involves cooling the printing surface and depositing droplets onto the cooled surface while the resulting printed object is maintained in air or a gas. Under these circumstances, the major mechanism of heat transfer is by conduction through the cooled surface. The heat is extracted from the change of phase interface, on the last printed layer, through the solid printed object to the cooled surface on which the printed object rests. Cooling the gas around the printed layer will have a minor effect, due to the low heat transfer coefficients between a gas and a solid. This limits the height of the printed object, because the freezing process cannot continue once the temperature of the last printed layer becomes lower than the phase transformation temperature. In addition, under these conditions of cryopreservation, cells will not experience optimal and similar freezing conditions in all the deposited layers. As the printing layer departs from the printing surface, the solidification interface will experience variable temperature gradients causing the morphology of the solidified material to change as a function of distance from the cooling surface.

In the case when printing is done by the release of droplets through a cooling fluid, the printed object is maintained below the freezing temperature, in a controlled way. However, the condition of the droplets is affected by the heat transfer and fluid flow as the droplet descends through the cooling fluid in an uncontrolled way. In particular, the Leiden frost phenomena will affect droplets as they descend through a cryogen at the phase transformation temperature, such as through liquid nitrogen. This method does not provide control over the deposited material at the deposition layer.

Printing using droplets that fall through a cooling liquid onto a printing surface have been attempted for several applications. For example, one approach at printing metal droplets used ethanol and water as the liquid through which liquid metal droplets fall onto the printing surface. However, premature freezing of the material blocking the distribution head is observed in this approach requiring the head to be heated. The descent of droplets through a liquid substantially decreases precision because of the complex nature of fluid flow of the liquid metal droplets as they descend towards the printing surface.

Accordingly, there is a need for systems, apparatus and methods for the controlled printing of objects with phase transition temperatures much lower than room temperature that can provide a variety of new, uniquely designed frozen and freeze dried products.

BRIEF SUMMARY

A major characteristic of 3D printing is the ability to control the macrostructure of the object. In the technology presented in this disclosure, this is achieved through drop-by-drop deposition or extrusions and incorporation of these additive elements at precise locations. In addition to control over the local macrostructure of the assembled object, the systems, apparatus and methods described herein also provide control over the local microstructure of the assembled object. There are applications of the 3D printing technology where precise control over the microstructure is essential and critical to the performance and characteristics of the generated object. The basic principle revolves around controlling the thermal, composition and geometrical parameters of the solidification process of each assembled element (i.e. drop) as it is additively deposited.

In various embodiments, the technology is embodied in fabrication systems, apparatus and methods for three-dimensional printing to incorporate printing of a printing fluid or melt onto a solid that is immersed in a temperature controlled liquid to produce an object. The methods ensure that the process of freezing is controlled precisely, and that the already printed frozen layers remain at a constant temperature. To illustrate the fabrication platform and methods, cryogenic 3D printing for freezing hydrogels is described that may have a game-changing impact on complex systems in tissue engineering. Complex frozen hydrogel matrix structures which contain functional cells and/or tissues can be generated when the 3D object is printed while immersed in a liquid coolant such as liquid nitrogen, while the upper liquid surface is maintained approximately at the same level as the highest deposited layer of the object.

Accordingly, the technology involves a continuous controlled change in the liquid level to correspond to the printing interface and has two important elements in this regard: (1) the entire printed object is at all times immersed in a temperature and composition controlled liquid from the base printing surface to approximately the printing interface of the growing object; and (2) the extent of the liquid region changes with the printing process so that at all times, as the printing continues layer deposited upon layer, the entire printed object always remains immersed in the fluid to approximately the printing interface.

In addition, control over the phase transition process is import to controlled manufacturing of 3D printed objects from a melt. The fabrication platform provides precise micro and macro control over the 3D printing by controlling conditions of the deposition of a solidifying liquid in three locations. Specifically, the platform provides: (a) control over thermal and fluid flow conditions of the molten material or fluid prior to phase transformation (Region 1); (b) control over the thermal conditions and thermodynamics during phase transformation at the interface (Region 2); and (c) control over the thermal conditions and stress distribution after the phase transformation within the pool (Region 3). Without control over the foregoing three regions simultaneously, however, it is not realistically possible to control the necessary precise microstructure of the 3D printed object.

The new technology can have a variety of applications and is particularly suited for generating tissue scaffolds with and without cells using 3D additive methods that employ precise control over the process of freezing, and thereby control over the microstructure of the frozen object. This is in addition to the control over the macroscopic structure that is inherent in the 3-D printing technology. The use of the freeze-drying process required to generate viable complex engineered tissue scaffolds while applying the new freezing technology demonstrates another utility of the technology.

One embodiment of the immersion cooling 3D printing apparatus has a printer head that delivers the material to be printed, in a molten form, at a controlled rate and temperature. The printing mechanism has the ability to move in the X-Y plane and the printing table can move on the Z-axis under computer control allowing for the manufacture of complex and precise shapes that are required in such a field as tissue engineering. The molten material is deposited by the dispenser on to the surface of the printing table where it solidifies. The process continues until a layer is completed, then the printing table moves downwards within the pool of cryogenic liquid and another layer is deposited.

The printed object is also maintained in a bath of liquid nitrogen or other cryogenic liquid whose height is continuously adjusted to maintain a predetermined distance from the deposition layer. The outcome of a freezing process during 3D printing can be substantially improved by immersing the 3D printed object in a liquid with a lower temperature than the phase transition temperature of the printed material. As consecutive layers are printed, the level of the immersion liquid should be continuously raised to be approximately flush with the highest printed layer i.e. the dispensing printing head.

In one embodiment the adjustment of the level of nitrogen is done by a simple valve and manual control. In another embodiment, the desired level of immersion liquid is maintained passively with mechanical or computer control. Several commercial devices exist for maintaining constant levels of cryogens or similar liquids. They employ solenoid valves attached to a sensor that detects the level of liquid nitrogen. Typical devices for maintaining a constant level consists of a self-pressurized liquid nitrogen Dewar and an on/off capacitive solenoid valve turns on and off the flow to the printing container. The fluid levels can also be monitored with infrared monitoring sensors, for example.

Control over the actions of the printer head, table positions and fluid levels are preferably provided by a controller such as a computer controller with software. The systems and apparatus preferably have a computer processor and a non-transitory computer-readable memory storing instructions executable by the computer processor for controlling the spatial and temporal position, temperatures and fluid flow from the printing head to deposit material according to a three-dimensional design and individual cross-sectional slices. The computer processor also monitors temperature and fluid level sensor data and may also have a display and user interface.

It can be seen that the systems, apparatus and methods can be used to produce a wide variety of printed objects depending on the materials and conditions that are used. For example, the printed objects can be natural and non-natural polymer-based scaffolds used for applications in tissue structures composed of cells and additives which stabilize the tissue matrices. The printed objects can be biomaterials such as collagen, chitin or other natural polymers-based scaffolds subject to freeze drying processes with a broad range of pre-defined cell compositions used as building blocks to design and construct complex organs.

The scaffolds can also include a variety of progenitor and stem cells and stem cell cocktails formulated in the presence of additives to ensure viability and functionality as complex multifunctional biotherapeutics. The produced objects also can be pharmaceutical compositions composed of biologically active protein subjected to freeze-dried processes. The same approach can be applied to food compositions. The produced objects can be single component and complex solid and liquid food materials.

According to one aspect of the technology, systems and apparatus are provided for cryogenic 3D printing using additive methods that employ precise control over the process of freezing, and thereby control over the microstructure and macroscopic structure of the frozen printed object.

Another aspect of the technology is to provide systems, apparatus and methods for producing frozen printed objects that allows control over thermal and fluid flow condition of the molten material prior to phase transformation, control over the thermal conditions and thermodynamics during phase transformation at the interface and control over the thermal conditions and stress distribution after the phase transformation.

Another aspect of the technology is to provide systems, apparatus and methods for cryogenic 3D printing that provides printing at a liquid dispenser interface with the object immersed in a pool of temperature controlled cryogenic liquid.

Yet another object of the technology is to provide systems, apparatus and methods for cryogenic 3D printing that can be used with a freeze-drying process to generate viable engineered tissue scaffolds, with and without cells, and other tissue scaffolds with controlled porosity and morphology that may be required for maintaining long-term and reproducible biological function.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Referring more specifically to the drawings, for illustrative purposes, embodiments of systems, apparatus and methods for cryogenic three-dimensional object printing are generally shown. Several embodiments of the technology are described generally in FIG. 1 through FIG. 4 to illustrate the printing systems, apparatus and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
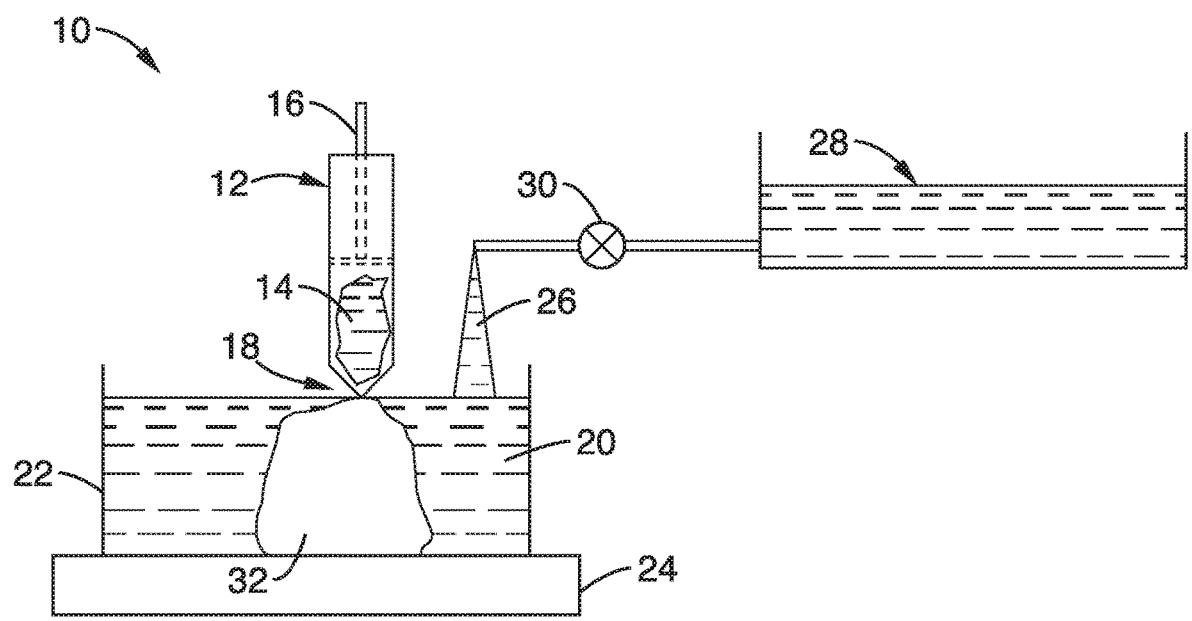
FIG. 1 is a schematic side view of a cryogenic three-dimensional printer apparatus according to one embodiment of the technology described herein.

Turning now to FIG. 1, one preferred embodiment 10 of a cryogenic 3D printing apparatus is represented conceptually. The apparatus 10 has a printing head assembly 12 that is configured for dispensing a fluid 14 and for X-Y positional translation and the container in which the object is printed. For clarity, the conventional motion carriage structures that facilitate the movement of the printer head assembly 12 in the X-Y plane or the vertical movement of the platform are not included.

The tip of the printing head is positioned at the surface of the cryogenic liquid to create a printing interface 18 that is at or below the surface of a pool 22 of cryogenic liquid 20. In the embodiment shown schematically in FIG. 1, the printing fluid 14 is extruded from the tip of the print head with a controlled plunger 16. The rate of extrusion through changing the position of the plunger 16 can be controlled by a controller. The size of the orifices at the tip can also be selected to produce a controllable volume emitted through the tip over time.

The printer head assembly 12 may optionally include temperature sensors coupled to a controller to monitor the temperature of the printing fluid 14 and allow the apparatus to maintain the fluid temperature to a selected temperature or temperature range. In addition, the printer head assembly 12 may optionally include pressure sensors to monitor fluid 14 pressure within the dispenser 12.

Although FIG. 1 shows a printer head assembly where the printing liquid is dispensed through single or multiple orifices such as a syringe, dispenser heads based on piezo driven inkjet printing technology can also be used. In this embodiment, the integrated piezo actuator induces a shockwave into the fluid contained in the head, which causes a droplet to be emitted from the nozzle.

The pool 22 of cryogenic fluid 20 is positioned on a platform 24 that can be moved vertically in the Z direction in the embodiment shown. The level of the surface of the pool 22 of cryogenic fluid 20 is preferably kept at a desired level with an intermittent stream 26 of cryonic fluid from a reservoir 28 of cryogenic fluid. Here the printed object 32 is maintained in a bath of liquid cryogenic liquid whose level is continuously adjusted to maintain a predetermined distance from the deposition layer. In this design, the adjustment of the level of cryogenic fluid such as nitrogen is done by a simple valve and manual control with a single valve 30. Control over the valve 30 is preferably performed with a controller.

In one embodiment, the desired level of immersion cryogenic liquid 20 is maintained passively with the use of level sensors. Several commercial devices exist for maintaining constant levels of cryogens or fluids. They generally employ solenoid valves attached to a level of liquid nitrogen sensor. For example, a self-pressurized liquid nitrogen Dewar is provided that has an on/off capacitive solenoid valve that turns on and off the flow of fluid to the printing container coupled to an infrared monitoring sensor to monitor fluid levels.

Other systems are microprocessor based systems that are designed to provide accurate and reliable level monitoring and dispensing control of virtually any cryogenic liquid. Microprocessor based electronics provide 0.1% readout accuracy. Nonvolatile, read only memory can maintain instrument calibration without battery backup. Watchdog timer circuitry and low line voltage (brownout) detector prevent microprocessor lockup and provide failsafe operation. Fill control and alarm functions are often provided.

In an alternative embodiment, a separate printing platform is provided that moves vertically within the cryogenic liquid 20 container 22. The platform 24 and container 22 remain in position while the separate platform moves in the Z-direction as directed by a controller to keep the platform and object printing surface at the proper position for the deposition of each layer of fluid 14 by the printer head 12.

Both the macroscale and the microscale characteristics of the printed object 32 can be controlled during the freezing process by immersing the 3D printed object in a liquid 20 with a lower temperature than the phase transition temperature of the printed material 32. As consecutive layers are printed, the level of the immersion liquid should be continuously maintained to be approximately flush with the highest printed layer, i.e., the printing interface. The printing interface 18 is the point at which the printing head touches the printed object, namely the location at which the process of printing takes place. It will be appreciated that the printed object 32 normally rests on a printing surface (support base), and that the level of the immersion liquid 20 has a height or distance in relation to the base printing surface of container 22. In this embodiment, the initial printing surface for the first deposited layer may be the bottom surface of the cryogenic liquid container 22 or may be a separate material positioned on the bottom surface of the container 22.

An important aspect of the technology is to immerse the entire region of the printed object, from the initial printing surface to the printing interface 18, in a liquid 20 with a controlled temperature (below or equal to the phase transition temperature of the printed object material). The cryogenic liquid 20 preferably has a composition that is optimized for preserving the printed object 32. For example, any kind of cryoprotective solution for cells such as the Wisconsin preserving solution or a solution with glycerol can be used.

Preferably, the level of the immersion liquid 20 is maintained at a level that is flush with the highest printed layer of the developing object 32. However, the fluid level does not have to be exactly flush, but can be approximately flush. For purposes of the description herein, the term "approximately flush" means preferably within +/−10%, more preferably within +/−5%, and more preferably within +/−1%, of the height (level) of the printing interface. In some applications a certain distance between the level of the fluid and the printing interface may be desired to achieve a certain temperature distribution in the printed object in order to affect the cooling rates of a droplet during the solidification process. In sum, the technology involves a continuous controlled change in the cooling liquid volume and composition to correspond to the printing interface.

Figure 2:
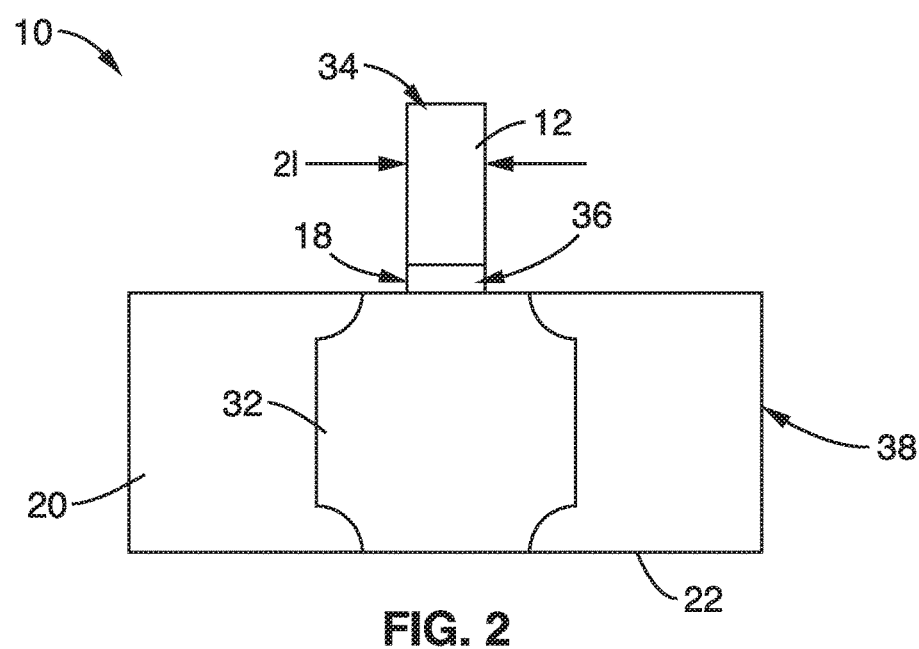
FIG. 2 is a schematic side view illustrating immersion cooling printing with three temperature control regions that allows control over where temperature over the solidification rate and consequently the microstructure of the printed material.

Referring now to FIG. 2, the phase transition process of the cryogenic printing apparatus is shown conceptually with the printer assembly and the container in which the object is printed. The realization of precise micro and macro control over the 3D printing through the deposition of a solidifying liquid is facilitated with control over three regions illustrated in FIG. 2. The present technology attempts to precisely control all three of these elements simultaneously.

The first region 34 is control over thermal and fluid flow conditions of the printing fluid 14 that is emitted from printing head 12 at the interface 18. Control over the temperature of the fluid 14 placed within the dispensing printer head 12 can be through temperature control over the source of fluid 14 and the dimensions and structure the printer head 12. In another embodiment, the printing head 12 includes a heating or cooling element that controls the fluid temperature. Temperature sensors in the printer head can assist with temperature control of fluid 14 in either setting.

The second region 36 for control is controlling the thermal conditions and thermodynamics during phase transformation at the interface 18 of the printer head and the level of the cryogenic fluid 20 pool in container 22. The third region 38 is control over the thermal conditions of the cryogenic fluid 20 within the container 22 where the object 32 is printed. Control over these three regions allows control over the precise microstructure of the 3D printed object.

There are two elements that are preferably optimized in Region 1 in the printer head 12 to facilitate control over the thermal and fluid flow conditions of the molten (fluid) 14 material (droplet) prior to phase transformation and to exert control over the 3D process. The first element is the formation and control over a temperature gradient in the printing material 14 in Region 1 at the phase transition interface. The second element is control over the composition of the selected printed material 14 that is expressed by the dispenser head 12 at the interface. To better control these elements, it is advantageous to have a one-dimensional temperature distribution in the printing material in Region 1, in a direction that is parallel to the change of phase interface.

This can be accomplished by ensuring that the Biot number in the narrow direction of the printing material in region 1 is smaller than one, where:

$$\text{Biot}=(h)(l)/k_f<1.$$

Here, h, is the heat transfer coefficient between the printing material in region 1 and the surrounding, l is half the typical dimension of the printing material in the first region 34 as shown FIG. 2 and $k_f$ is the thermal conductivity of the printing material in the first region 34 (Region 1).

Ideally the viscosity of the printing material 14 in Region 1 is typically much larger than that of the surrounding fluids while sufficiently fluid for printing at a desired rate. Control over the fluidity required for printing could also be achieved by adding a heating/cooling element to the printing head 12 at Region 1, which can control the temperature of the printing material 14 in that region of printing head 12. Similarly control over the deposited material 14 can be achieved through control over the volume of a dispensed droplet and the speed with which the droplet impinges the printing interface.

Control over the second region 36 (Region 2) at the interface between printer head 12 and the cryogenic fluid 20 level is important for controlling the microstructure of the printed object 32. There are several elements that govern the process. In pure material it is the temperature (T) gradients in the liquid (l) and solid (s) parts and the change in enthalpy upon phase transformation (L):

$$k_l\frac{\partial T_l}{\partial n} - k_s\frac{\partial T_s}{\partial n} = \rho L V$$

where n is the direction normal to the change of phase interface, ρ is density and V is the rate of phase transformation. In the case of cryogenic 3D printing, the rate of phase transformation is also dictated, in addition to the thermal and fluid flow aspects, by the velocity of the printer head and the rate of flow of the printing material from the head. The equation above is for the case of a pure material with a distinct phase transformation temperature. When a more complex material is used, such as glycerol in an aqueous solution, the phase transformation occurs over a range of temperatures and the parameters listed here need to be controlled in the entire range.

The situation at the second region 36 is further complicated in cases where cells are deposited during printing with freezing. The survival of cells during phase transformation depends on several parameters, such as the composition of a cryopreservation solution and the cooling rates during freezing. Therefore, the rate of deposition and the temperature gradients should be optimized with the cryopreservation process in mind. In addition, when the microstructures of object 32 are important, the nucleation of the molten liquid and the crystal orientation in the solid play an important role in the structure of the final product.

The third region 38 (Region 3) is the controlled temperature liquid that engulfs the printed object 32. There are two important elements in this region 38. One is the temperature gradients at the change of phase interface 18. Control over the temperature of the pool of cryogenic liquid 20 in container 22 can be accomplished by controlling the temperature of the liquid at the source and periodically adding or replenishing the liquid within the pool.

The second element is the preservation of the manufactured product 32. Ignoring the second element can lead to the degradation of the manufactured product 32 while the manufacturing process is still taking place such as the melting of the printed ice cream or the death of cells during the printing of higher layers. To avoid degradation, the printed object 32 is immersed into a liquid 20 that has the optimal composition and temperature for preservation while the manufacturing process occurs. For instance, if the phase transformation temperature is the freezing temperature, printed cells would survive longer periods if the printed object is immersed in a preservation solution that is preferably at or below the printed object phase transition temperature (freezing), as the printing occurs. If there is freezing, the printed object could become immersed, as it is printed, in a fluid that is at or below the freezing temperature to maintain constant temperature and optimal conditions of preservation. This cooling liquid 20 can be liquid nitrogen as in the examples described below.

It should be emphasized, that when high temperature gradients occur in the solid object 32, the object may experience high thermal stresses, and therefore immersion in a constant temperature liquid 20 is beneficial.

A variety of different liquids could be used as the cooling immersion liquid 20 that is used to immerse the manufactured printed object 32 during, and after the layered production process steps occur. Liquid nitrogen may be an optimal liquid for tissue engineering. However other options are also possible. For example, a cryoprotective mixture of water, extracellular or intracellular salts and glycerol could be chosen to protect freezing cells from low temperature storage damage.

In the case of ice cream, for example, a mixture of water and sugar with a phase transition temperature lower than that of the product could be used as the immersion liquid 20. A mixture of water and alcohol could be also used, for instance for frozen food products that involve alcohol.

There are two important additional elements that may be considered for the printing of freezing materials to exert control over the microstructure of the final object 32. One is a nucleating agent. This is important in particular at the beginning of the printing process. The nucleating agent is also important throughout the printing process as each additional layer is added. Normally, the previous layer serves as the nucleating agent. However, nucleation agents may be added when the structures involve different materials. Chemical additives with a particular crystalline structure, and/or particular physical properties, and/or biological properties may be added to the printed material. An example is ice nucleating proteins.

A second important element for consideration in optimizing the printing process of aqueous solutions is the recrystallization during storage or even during printing. This could substantially alter the microstructure of the printed product. One way to eliminate recrystallization is by adding chemical species that inhibit recrystallization. Antifreeze proteins are well known as an effective material that inhibits recrystallization. The antifreeze proteins, such as AFGP or AFP1 can be added in small quantities, such as from 1 mg/ml to 0.001 mg/ml, to the printed material 14. Their anti-ice recrystallization effect may be essential in printing frozen material for storage in a frozen state such as in the case of frozen foods without affecting their quality.

The printer assembly illustrated in FIG. 1 and FIG. 2 is preferably part of a system 40 with a cryogenic fluid supply and control subsystems. In the embodiment of the system shown in FIG. 3, the printer assembly 42 has a printing head that is attached to a carrier that can move the dispenser head in the X-Y plane. The printing surface also has a controlled carriage to move the printing platform vertically in the Z-direction. The printer assembly 42 also has a dispensing head with controlled extrusion rate, volume and temperature. The printer assembly 42 also has a fluid filled container with a printing surface.

The system 40 also has a control subsystem with a computer 44, display 46 and interface keyboard 48 that has software for controlling the supply of cryogenic fluid to the system as well as the actions and functions of the printer assembly 42. Both the X-Y motion and the dispensing conditions of the dispenser head are computer controlled. The printing surface also has computer control over the carriage to move the platform in the Z-direction.

The computer 44 is also connected to the cryogenic liquid supply and controls the cryogenic fluid from a liquid source 64 with control of valve 62 on fluid line 66 by control a line 60. The valve 62 may be partially or fully opened by computer 44 programming to deliver desired volumes of cryogenic immersion liquid to the printer 42 elements.

The computer 44 also receives signals from temperature, pressure or level sensors of both the cryogenic supply and the printer sensors. For example, the immersion fluid temperature of the printer should be controlled and should be lower or equal to the freezing temperature of the printed object material. The immersion fluid level also changes during the printing process to continuously match the top of the last printed layer. The valve 62 separately or in addition to valve 30 of FIG. 1 may be used to meter the addition of the immersion liquid to the printing pool container to maintain the desired level as shown in FIG. 1.

The computer 44 monitors and controls the conditions of the three regions identified in FIG. 2, preferably through sensors and control software. The printer assembly 42 may employ level sensors, temperature sensors and rate sensors in association with solenoid valves that are operably attached to the computer 44. A sensor detecting the level of liquid nitrogen, such as an infrared monitoring sensor, may also be used. The cooling liquid of supply 64 can be liquid nitrogen. However, the same design is possible with other cooling liquids such as Freon or a solution of ethylene glycol or an aqueous solution with sugar or salt or an alcohol.

The computer 44 software also has control over the printing actions of the printer assembly 42 through control line 68. The software of computer 44 translates a three-dimensional digital design file into physical objects by controlling the X-Y-Z positions of the printer carriage and platform and the dispensing head emissions. The computer control system 44 programming generates layer data by slicing, varying layer thickness, rounding, filling and scaling. The programmed cross-sectional patterns provide position and emission commands for each successive layer of material that is disposed on the printing platform or object.

The 3D printing approach described herein has several key benefits for freezing in general, and tissue engineering in particular. First, because the manufactured object is maintained at a constant temperature below freezing, the possibility of local melting is eliminated and this allows the generation of larger and more complex biological-based structures by the printer 42. Furthermore, it eliminates thermal stresses and precisely defines the thermal conditions at the change of phase that defines the microscale structure of the frozen object. Elimination of thermal stresses can be a key element in maintaining the integrity and stability of biological materials which constitute the engineered tissue.

Accordingly, the technology generates the engineered tissue or organ scaffolds already in a frozen state, and therefore the scaffolds are already preserved at the time of manufacture. In addition, it should be possible, when the engineered tissue is seeded with cells, to design protocols to optimize the cryopreservation of cells. In fact, this technology should be able to generate by vitrification very rapid freezing when printing with small droplets, and thereby, preservation of cells in a large complex organ in a vitreous state. The freeze-drying process based on the freezing procedure enables manufacturing of cell-based tissue scaffolds with the desired biological properties and the required product stability. The scaffold provides the necessary physical porous infrastructure which allows population by the required cells. These scaffolds are typically built from biopolymers and have properties of hydrogels such as agar or collagen.

The system, apparatus and methods can enable a variety of applications in life sciences and biotechnology. For example, the apparatus can be used to engineer stable tissue scaffolds, with or without cells, as well as with complex multi-drug delivery mechanisms and food technology applications.

In the field of tissue engineering, the manufacturing strategy is comprised of two steps. First the engineered scaffold or tissue is designed and produced. Then, techniques for long term preservation of the product are employed such as by freezing. With the present methods, the engineered tissue is produced in a frozen state, ready for long term storage, thereby eliminating a complex step in the manufacturing process of engineered scaffolds.

The drying process which has been applied to a broad spectrum of applications is often used to generate long-term stable scaffolds that can be used at a later stage as desired. In a proof-of-feasibility, agar was used as the printing materials and liquid nitrogen as the immersion fluid. Liquid nitrogen is convenient because it maintains a constant temperature at atmospheric pressure, without the need for controls. However, other aqueous printing materials and immersion fluids can be used as well. In fact, the immersion cooling liquid can be a preserving solution or a cryoprotectant solution and the printing material can also be a (stem) cell.

It should be appreciated that this technology could be used in other aspects of tissue engineering as well. Currently, attempts are made to incorporate cells, such as stem cells, into engineered tissue scaffolds. The technology described herein may be suitable for 3D printing of tissue scaffolds which contain cell cocktails and tissue combinations that are required to enable replacement of natural complex biological processes and systems.

Cryopreservation of cells by rapid freezing in small volume droplets is known in the art. The cryogenic 3D printing method described herein could be used to produce cooling rates typical of splash freezing, and may result in vitrification of cells. While it is not possible to cryopreserve whole organs at the present time, cryopreservation of single cells is routine and well known. Since in this technology each cell is frozen separately under controlled conditions of composition and temperature control, the vast knowledge of cryopreservation protocols can be incorporated into this technology to optimize the freezing of each cell in the structure that is formed.

The described technology can be uniquely applied to the emerging field of generating complex tissues and organs based on a mixture of printed scaffold, cells and stem cells. The scaffolds produced in a very controlled and custom designed freezing, thawing, and freeze drying process which generates controlled porous micro- and macro-structure, enables nutrients and factors to perfuse the structure, plus incorporates additional new type of cells to be accessible to the newly generated tissue and eventually the newly generated organ. This technique enables the use of predesigned compositions of continuously viable stem cells having the right properties and which are used as mini cell factories to generate viable replacement organs.

The precision achieved by the technology throughout the freezing, thawing, and freeze-drying steps, and the unique technology concept is a breakthrough as it enables a diverse repertoire of viable and fragile cell combinations to act in "harmony" as nano-factories and in a timely fashion to generate within the scaffold functional yet complex tissues.

Moreover, the described 3D freezing method combined with drying step, enables the construction of multi-layered scaffolds where each layer contains a repertoire of different cell compositions possessing unique properties desired and needed to construct complex biological structures and functions such as multi-cell type organoids. The emerging area of stem cells-based medical applications can particularly take advantage of the described technology.

Another important field in life sciences is the field of drug delivery and the combination of medical devices with pharmaceuticals to achieve an optimally targeted, and timely exposure of the active drug, biologics, or cell factories to generate a certain biological agent that is deficient in the patient. The 3D printing apparatus and technique enables the generation of precise freeze-dried drug delivery systems and drug-based devices which can be used in a variety of settings including polymer-based or other highly porous implants which have large surface areas. The implants can be manufactured to resemble implants currently used by the pharmaceutical industry with the major distinction being that the implant generated by the described 3D invented printing method would have a higher payload capacity, would be much more versatile, and enable the use of a more complex mixture of biological unstable materials and biologics.

In the field of food technology, the technology described in this disclosure could produce a structure made of ice cream or other frozen food products, such as frozen yogurts or sorbets, with a precisely determined configuration, texture and taste. The key aspect is the ability to control the microstructure. Small ice crystals are of value in defining the quality of ice cream or other frozen confections. This technology can control the microstructure of the frozen product, as well as the macrostructure. Other frozen food products can be designed with this method, such as frozen dough or frozen fast food combinations. Frozen composites can be also produced.

Accordingly, the apparatus and methods for 3D printing of frozen objects have a wide variety of potential applications in tissue engineering, medical devices and pharmaceuticals and food technology. It has been shown that the simple immersion of the printed object in a cooling liquid, with a variable height fitted to the last printed layer, can produce high reproducible quality and rapid printing of frozen objects, as well as, freeze-dried objects.

The technology of this disclosure may be better understood with reference to the accompanying examples, which are intended for purposes of illustration only and should not be construed as in any sense limiting the scope of the presented technology as defined in the claims appended hereto.

Example 1

Figure 3:
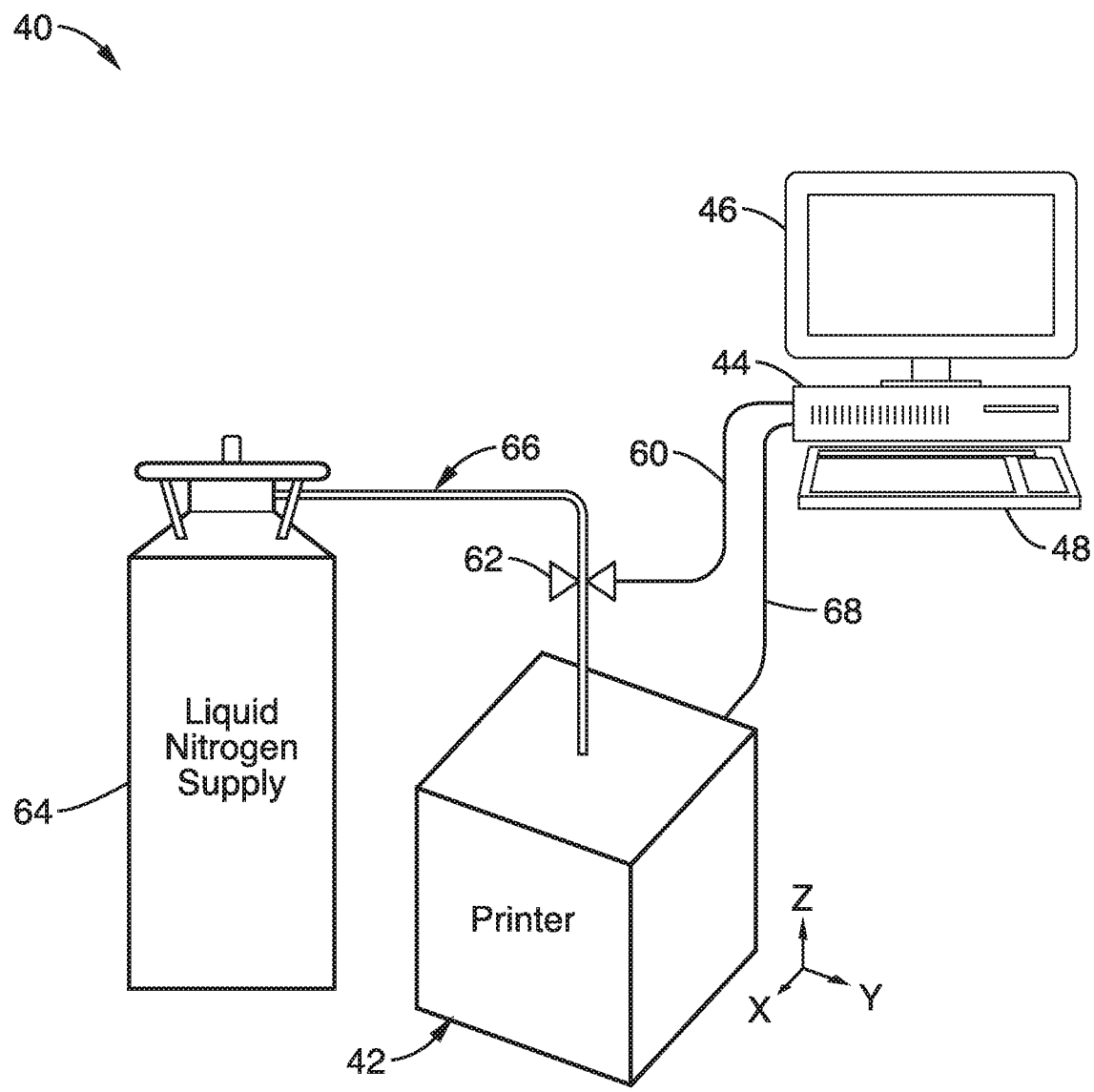
FIG. 3 is a schematic front view of a printing system showing printer, cryogenic liquid source and computer controller according to one embodiment of the technology described herein.

In order to prove the concept of the 3D printing apparatus and methods of use, an apparatus was produced using the general design of FIG. 3 and tested. To demonstrate the technology, a conventional 3D printer (FlashForge, Creator Model, and Los Angeles, Calif. USA) was modified. The original printer head that is configured to melt and disperse a plastic was replaced with a new printer head assembly. The printing head carriage that is capable of controlled X-Y movements remained.

In addition to a new printer head, a glass dish was placed on top an insulation layer on the printing table of the printer. It served as the container for the immersion fluid and the printed object. The immersion fluid addition to the dish was done manually.

The new printer head was centered on a syringe, loaded with a hydrogel that was liquid at room temperature as the printing material. The plunger of the syringe dispenser was controlled by a NEMA17 stepper motor. The stepper motor was taken from the original printer where it dispersed the molten plastic under computer control. In this design the rate of hydrogel delivery onto the printing surface first and later the object printing interface, was controlled by the printer software. The printing head components were attached to a 3D printed assembly frame. The assembly frame was designed to attach to the original X-Y printer head carriage, at the same location and in the same way as the original printing head. This also allows the use of the original software to control the X-Y motion of the new printer head, without any modification. Optionally the temperature of the printing hydrogel inside of the syringe was controlled through resistive heating, to ensure the desired temperature and viscosity. Agar gel in distilled water, 40 g/l was used as the printing fluid, and liquid nitrogen was used as the immersion constant temperature fluid.

Blender software was used to create 3D models in STL format. The Slic3r software program was used to convert them into GCODE instructions which were translated by GPX into X3G files for use on the 3D printer. The Flash-Forge printer was also running the preinstalled Sailfish Firmware.

For comparison, several printings were performed outside of the cryogenic pool. Several different failures of the 3D printing by freezing to illustrate the value of the simple but central concept of printing in an immersion cooling liquid. The results of printing through gaseous nitrogen cooled air onto a liquid nitrogen cooled printing surface were unsatisfactory. The results demonstrated that with this mode of cooling, higher layers of the 3D printed object cannot solidify, and, therefore, the ability to print large organs is limited.

A computer controlled 3-D printing of a freezing object with computer control over the X-Y-Z motion and with the use of an ice nucleating layer and immersion of the printed object in liquid nitrogen was also performed and compared. The layers were printed precisely one on top of the other and the top layer is as solid as the bottom layer.

The illustrated printed framework could become a large blood vessel, with precisely computer controlled composition and structure. An important aspect of printing frozen structures related to ice nucleation was also observed. Nucleation is an important aspect of solidification of small droplets in particular. It was observed that an ice nucleating layer (seed) was required to initiate the frozen object printing process.

In one illustration, a tissue paper saturated with water and frozen on an aluminum sheet in liquid nitrogen was used as the nucleation source on the printing surface. In addition to serving as a nucleation site, this configuration secured the printed object to the printing surface, preventing it from floating away in the immersion fluid. The object was printed under a layer of liquid nitrogen that was maintained approximately flush with the highest layer of the printed object.

It was demonstrated that the simple immersion of the printed object in a cooling liquid, with a variable height fitted to the last printed layer, can produce high quality and rapid printing of frozen objects. It will be appreciated that the method for 3D printing of frozen objects will have potential applications in tissue engineering and freeze-drying as applied to medical devices and pharmaceuticals and food technology.

Example 2

To demonstrate the functionality of the apparatus and methods, the 3D cryoprinting methods were applied to lyophilization and the formation of "freeze-dried" scaffolds. Lyophilization, also known as freeze drying, is a process commonly used to stabilize products such as biological materials, including biological drugs such as monocolonal antibodies, that would otherwise quickly degrade. Use of the lyophilization process is widespread in industries such as pharmaceuticals, biotechnology and the food industry. Lyophilization also holds great promise for regenerative medicine and tissue engineering. The prospect of preserving valuable scaffolds with or without cells in a freeze-dried form has substantial value for the development of multicomplex scaffolds which would be used in generating organs.

Figure 4:
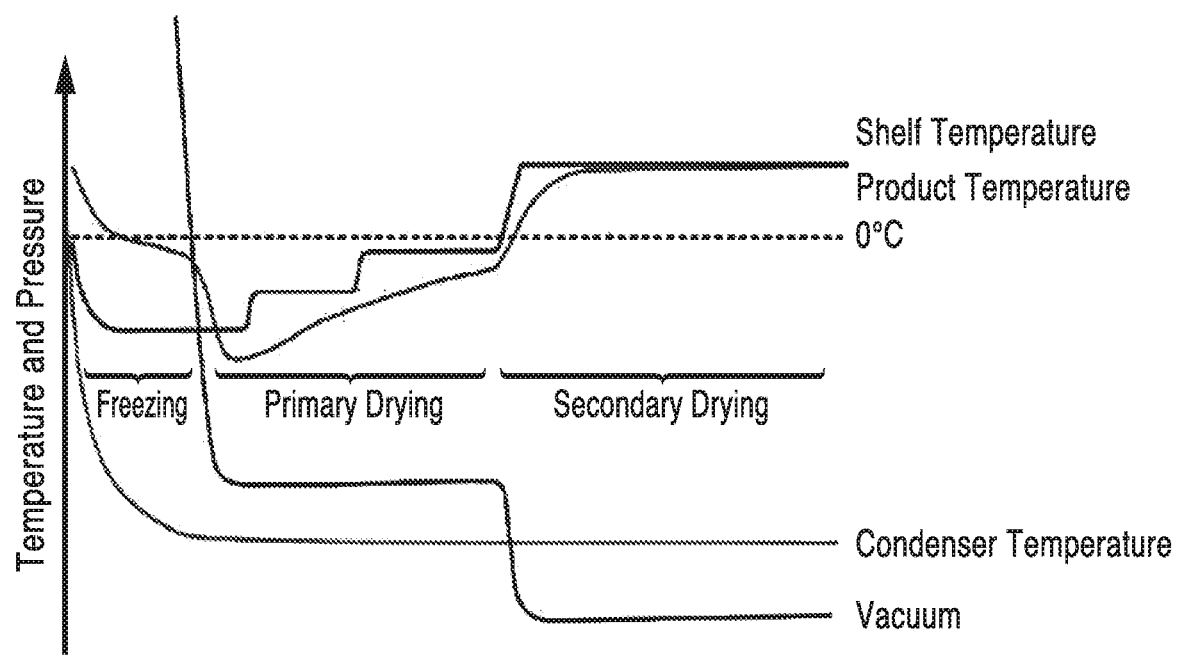
FIG. 4 is a graph of temperature and pressure over time of the process events of freeze-drying (lyophilization).

Lyophilization is a standard procedure that takes place in three typical stages: 1) freezing, 2) primary drying, and 3) secondary drying to produce a final product as shown in FIG. 4. However, one major drawback of the process is that ice crystals formed during uncontrolled freezing during the first stage can produce suboptimal pores and damage or destroy cells that are incorporated into the scaffold. The successful and accurate production of bio scaffolds by lyophilization therefore demands control over the pore size, in the range of micrometers, and pore consistency throughout each sample. It also requires optimal freezing of cells in the scaffold in the event that freeze drying of printed cells is desired. Scaffold structures are tissue specific and therefore, the size of the pores must be accurate and relevant to the tissue of interest. Achieving the optimum texture and porosity of the sheets is essential to support and encourage the body to generate new cells as quickly as possible, and to ensure the desired type of cell structure.

The first stage in lyophilization is for the sample to be frozen as seen in FIG. 4. As mentioned above, the manner of freezing determines the crystalline structure. The freezing step of conventional techniques is performed by freezing the entire bulk of the material. The challenge is to be able to control the freezing conditions in such a large volume sufficiently to achieve the desired result in terms of the ice crystal structure. The pores in the final scaffold are a by-product of the freezing process since the ice crystals formed during freezing leave holes in the structure when the sample is dried.

In the case of collagen bioscaffolds, for example, the range of desired pore size is in the micrometer range. Similarly, endothelial cells in blood vessels have been shown to grow optimally with a scaffold with a pore size of 20 µm to 80 µm, whereas osteoblasts require pores larger than 100 µm for bone formation. Therefore, control of the dimensions of the ice crystals that are grown is critical to the successful and accurate production of bio scaffolds.

Another important element is the distribution of the pores in the tissue. It is virtually impossible to control the macroscopic distribution of the pores with conventional methods. For example, when the sample is frozen in bulk, any variation in the temperature as the sample is frozen results in a change in freezing rate and therefore a variation of pore size throughout the lattice. Once frozen, the sample is kept below its critical temperature so that it stays in a frozen state while a moderate vacuum is applied. The pressure/temperature balance is adjusted until it reaches the triple point so that the ice sublimes straight to a vapor without going through the liquid phase. Sublimation leads to evaporative cooling, which further lowers the sample temperature. To maintain the sample at a constant temperature, heat must be applied to compensate for sublimation cooling. This primary stage requires exquisite control over the temperature of the sample.

Secondary drying is a desorption process that removes any water that is chemically bound to the lattice. Desorption drying is achieved by raising the temperature of the sample and reducing the chamber pressure to a minimum. The moisture level at this stage may be around 5% to 10%. Depending on how dry the end product needs to be, secondary drying may be a long and slow process. In the case of a protein such as collagen, care must be exercised. While polymerization during water removal is required to form the cross-linked structure to create a stable sponge, higher temperatures in secondary drying may result in biodegration of the sample. Important applications are in the formation of cartilage replacements for the knee.

In contrast, the 3D cryoprinter and methods provided control over the macrostructure and microstructure of the freeze dried product. Through control of the delivery of the printed material and its composition as well as thermal control over the three regions described above it was possible to achieve control over both the microscale shape of the scaffold and the structure and dimensions of the pores. The 3D cryoprinting technology overcomes a major hurdle in lyophilization technology which is the controlled formation of the ice crystals and control over both the macroscopic and microscopic morphology.

As shown previously, the desired macroscopic configuration and the microscopic structure can be obtained by controlling the deposition of each droplet as well as the composition of each droplet and the temperature history. The microstructure of the object can be controlled by the droplet size, printing layer temperature, composition and shape. Whereas conventional methods for producing scaffolds have frozen the entire structure, the methods and apparatus allowed for the optimal freezing of each individual droplet under controlled conditions.

A variety of biopolymers for scaffolds can be used in addition to alginate such as collagen-based scaffolds, chitin, fibroin etc. which are also acceptable by the FDA. The cross-linker used for these polymers may also be important and may control the pore size and thickness to some degree. Typically cross-linking can be done either before or after freeze-drying. The range of freezing is typically between 20° C. to minus 70° C. Drying was typically done in a two-step process where temperature is raised based on pre-selected cycles which typically take 48 to 72 hours to complete depending on the properties required for the scaffolds such as porosity. Mean pore sizes which are crucial to a particular application in tissue engineering can be within the range of between approximately 30 microns to 350 microns, Pore size and distribution are often the most critical parameters determining the viability of cellular activity in structures.

Furthermore, it becomes possible with 3D cryoprinting to form lumens for producing conduits for flows, or for optimizing the freeze drying process. These lumens can be formed by several methods. One is by actually printing around the spaces that should serve as the lumens. Structures with lumens that could be conduits for blood flow, for example, were 3-D cryoprinted and then freeze dried. Another technique for producing designated conduits involves the use of two 3D printing heads, one with the gel and the second with pure water. The structure designated for an open lumen can be printed with pure water drops, while the structure designated for a tissue scaffold can be printed with the gel droplets. After freeze drying, the volume 3D printed with pure water becomes an open lumen. Of course additional printing heads can be added to the process which would enable delivering either different local compositions or cells encapsulated in the gel.

Example 3

To further demonstrate the functionality of apparatus and methods, scaffolds made from collagen were created. Collagen is a protein used by the body for cartilage tissue generation, and is a major component of connective tissue in mammals. Collagen is used widely in tissue engineering, often as a bioscaffold. It is readily available from animals, and its acellular structure can be manipulated to form porous scaffolds of varying structure and porosity. The type of collagen (Type I or Type II) that is used depends on the particular required application.

Conventional collagen scaffolds are typically produced by isolating collagen from bovine or porcine sources that is chopped to the required length and dissolved in a solvent such as acetic acid or hydrochloric acid. Water is added to create an emulsion. Using a conventional method the emulsion is frozen by placing it in a metal mold and immersing it in liquid nitrogen. During freezing the solution forms ice crystals in the structure. Finally, the frozen emulsion is lyophilized to remove the ice crystals, leaving a collagen sponge with the required matrix of pores. The removal of water during this stage of lyophilization results in intermolecular cross-linking between the collagen strands to form a stable collagen scaffold matrix.

Using the technology described herein, the collagen was loaded in the syringe as shown in FIG. 1 and the structure was frozen with the desired macro and microstructure. This was followed by a standard freeze-drying protocol adjusted to the composition and size of the product. Furthermore, the frozen structure made by the 3D cryoprinting was already immersed in liquid nitrogen and could be transferred directly to the drying process.

Example 4

A scaffold made from alginate was produced to demonstrate the use of the apparatus and methods with other scaffold printing materials. The material that was used for printing was a solution of a cross-linked alginate gel (a high water-content hydrogel) derived from brown sea algae (Pronova Biopolymer). The alginate gel was a linear block copolymer of 1-4 linked α-L-guluronic and β-D-mannuronic acid units, with the guluronic content dictated the strength of the gel. In order to increase this mechanical strength, the alginate gel was cross-linked with calcium gluconate ($Ca^{2+}$). The cross-linking occurred when the divalent cations bind with the glucoronic blocks forming a binding region. The concentration of calcium gluconate had a large impact on the gel network strength. For this reason, a probe sonicator was utilized in the cross-linking process to ensure that a homogeneous composition was achieved.

To create the printing solution, a combination with a ratio of two grams of alginate powder (composed of 65% to 75% guluronic acid units) to 100 ml of distilled water was mixed using a magnetic stir bar to homogenize the alginate gel. A magnetic stir bar was also used to create the cross-linker solution composed of a ratio of two grams of calcium gluconate powder to 100 ml of distilled water. In creating the final solution, a probe sonicator was utilized to homogenize 10 ml of the alginate gel with 8 ml of distilled water. Following this, the cross-linker solution was added, drop-by-drop, from a syringe into the alginate gel solution, while the probe sonicator acted to homogenize the mixture. Following the preparation of the solution it was loaded into the syringe as shown in FIG. 1 and then 3-D cryoprinted. The resulting printed object had the desired micro and macroscale morphology. Immediately following the controlled freezing procedure, the sample was placed into a styrofoam box containing liquid nitrogen. It was held in the vapor of the liquid nitrogen until it could be placed in the freeze dryer. Each sample was exposed to one drying cycle in a Labconco flask freeze-dry system, and held at a temperature of −43° C. and pressure of $227 \times 10^{-3}$ Mbar for approximately 1 hour.

Example 5

Controlled cooling rate droplet printing was simulated to demonstrate cryoprinting as a function of the distance between the top level of the cooling fluid and the top level of the printed layer. In cryoprinting, droplets of gel or gel with cells are printed onto the upper surface of an object immersed in a cooling fluid and liquid nitrogen was used in this example. The cooling rate affects the microstructure of the frozen gel and the survival of the cells, with higher cooling rates generating smaller ice crystals and lower cooling rates required for survival of cryopreserved cells with lower levels of cryoprotectants. A controlled rate of cooling can be achieved by exercising control over the distance between the level of liquid nitrogen and the printing surface.

In this simulation, a frozen gel structure is present in a bath of cryogenic liquid that could have been obtained by direct printing in the liquid. A drop with a cell in it will be frozen on the top layer of the printed object, and precisely prescribed cooling rate for this drop is desired for this purpose. A distance H is generated between the top layer of the frozen printed gel and the liquid nitrogen bath (this can be obtained for instance by removing the liquid nitrogen or letting it evaporate.

At steady state, when the system is in air, a linear temperature distribution occurs in the frozen gel between the temperature of liquid nitrogen $T_{LN}$ and the freezing temperature of the gel $T_{FZ}$. When a droplet is deposited on top of the frozen gel, the heat is extracted through the frozen gel of height H and thermal conductivity, k.

From conservation of energy, the rate of freezing is given by:

$$q = -k\frac{\partial T}{\partial x} = \rho L \frac{dH}{dt} \qquad (1)$$

where, L is the latent heat of fusion and H the distance between the top of the gel and the top of the liquid nitrogen.

Assuming a quasi-steady temperature profile (large change in enthalpy with phase transformation), then:

$$\frac{\partial T}{\partial x} = \frac{(T_{LN} - T_{FZ})}{H} \quad (2)$$

and $$-k\frac{(T_{LN} - T_{FZ})}{H} = \rho L \frac{dH}{dt} \quad (3)$$

Equation (4) gives the expression of the cooling rate of the freezing droplet (dT/dT), as it comes in contact with the frozen gel as a function of the rate of propagation of the freezing interface and the temperature gradient in the solid gel (Transformation from an Eulerian system to Lagrangian system).

$$\frac{dT}{dt} = \frac{\partial T}{\partial x}\frac{dH}{dt} \quad (4)$$

Combining equations (2), (3) and (4) gives a first order estimate for the cooling rate during the freezing of the droplet, as a function of H and the thermal properties of the freezing gel as follows:

$$\frac{dT}{dt} = \frac{k}{\rho L}\left\{\frac{(T_{LN} - T_{FZ})}{H}\right\}^2 \quad (5)$$

From equation (5) one can obtain the distance, H, between the frozen gel upper surface and the liquid nitrogen surface to achieve the desired cooling rate (dT/dt) during the freezing of the droplet. It is evident that the cooling rate of every small droplet can be designed as a function of H, the distance between the top level of the printed surface and the top level of the cooling fluid and the thermal properties of the frozen object. This solution is for the case in which the dimension of the drop is much smaller than the dimension of the frozen object. For other situations, the complete detailed solution of the process of freezing needs to be employed. Available computer programs, such as COMSOL, can be used for calculating an exact solution, in one embodiment.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. An apparatus for cryogenic 3D printing of an object from a fluid, the apparatus comprising: (a) a printing head assembly with a dispenser configured for dispensing a fluid and for X-Y positional translation; (b) a cryogenic liquid container having a printing surface, said container and printing surface configured for Z positional translation; (c) a cryogenic liquid disposed within the liquid container; and (d) a control mechanism operably coupled to the printing head assembly and, cryogenic liquid container, the control mechanism configured for: (i) dispensing the fluid material onto the printing surface and moving the printing head assembly with X-Y position translation to form a layer of a 3D printed object; and (ii) moving the cryogenic liquid container and printing surface with Z position translation and repeating step (i) to print multiple layers, wherein a previously printed layer serves as the printing surface for a subsequently printed layer; (iii) wherein as each layer is printed, the entire printed object to the last printed layer is immersed in cryogenic liquid held within the cryogenic liquid container.

2. The apparatus of any preceding embodiment, further comprising: a source of cryogenic liquid; a conduit coupled to the source of cryogenic liquid; and a valve joined to the conduit configured for dispensing cryogenic liquid from the source of cryogenic liquid into the cryogenic liquid container; wherein cryogenic liquid levels in the cryogenic liquid container are controlled with actuation of the valve.

3. The apparatus of any preceding embodiment, wherein the dispenser of the printer head assembly comprises: a syringe body with at least one orifice; and a moveable plunger within the syringe body; wherein controlled movement of the moveable plunger will dispense fluid from the syringe body through at least one orifice.

4. The apparatus of any preceding embodiment, said controller further comprising: (a) a computer processor; and (b) a non-transitory computer-readable memory storing instructions executable by the computer processor; (c) wherein said instructions, when executed by the computer processor, perform steps comprising: (i) dispensing the fluid material onto the printing surface and moving the printing head assembly with X-Y position translation to form a layer of a 3D printed object, said material having a phase transition temperature, the printing surface having a temperature lower or equal to the phase transition temperature of the material; (ii) moving the cryogenic liquid container and printing surface with Z position translation and repeating step (i) to print multiple layers, wherein a previously printed layer serves as the printing surface for a subsequently printed layer; (iii) wherein as each layer is printed, the entire printed object to the last printed layer is immersed in cooling liquid held in the constant temperature liquid container at a temperature that is lower or equal than the phase transition temperature of material; and (iv) continuously raising the level of the cooling liquid in the constant temperature liquid container so that the liquid level is maintained at a level that is approximately flush with the surface of the last printed layer.

5. The apparatus of any preceding embodiment, wherein said instructions when executed by the computer processor further perform steps comprising: sensing a cryogenic liquid level in the cryogenic liquid container; and allotting a volume of cryogenic liquid to the cryogenic liquid container to maintain a set level; wherein the cryogenic liquid level is maintained at a level that is approximately flush with the surface of the last printed layer.

6. The apparatus of any preceding embodiment, wherein said instructions when executed by the computer processor further perform steps comprising: providing a three-dimensional object design of cross-sectional slices to define the respective layers for construction by the apparatus; and dispensing fluid with the dispenser on the printing surface according to each cross-sectional slice of the object design.

7. The apparatus of any preceding embodiment, wherein said instructions when executed by the computer processor further perform steps comprising: sensing the temperature of the fluid in the printing head assembly; controlling the temperature of the fluid dispensed from the printing head assembly; controlling the cooling rate of the printed layer; and controlling the temperature of the cryogenic liquid in the cryogenic liquid container.

8. An apparatus for cryogenic 3D printing of an object from a fluid, the apparatus comprising: (a) a printing head assembly with a dispenser configured for dispensing a fluid and for X-Y positional translation; (b) a constant temperature liquid container having a printing surface, said container and printing surface configured for Z positional translation; (c) a cooling liquid source; (d) a valve configured for dispensing cooling liquid from the cooling liquid source into the constant temperature liquid container; and (e) a control mechanism operably coupled to the printing head assembly, constant temperature liquid container and valve, the control mechanism configured for: (i) dispensing the fluid material onto the printing surface and moving the printing head assembly with X-Y position translation to form a layer of a 3D printed object, said material having a phase transition temperature, the printing surface having a temperature lower or equal to the phase transition temperature of the material; (ii) moving the constant temperature liquid container and printing surface with Z position translation and repeating step (i) to print multiple layers, wherein a previously printed layer serves as the printing surface for a subsequently printed layer; (iii) wherein as each layer is printed, the entire printed object to the last printed layer is immersed in cooling liquid held in the constant temperature liquid container at a temperature that is lower or equal than the phase transition temperature of material; and (iv) continuously raising the level of the cooling liquid in the constant temperature liquid container so that the liquid level is maintained at a level that is approximately flush with the surface of the last printed layer.

9. The apparatus of any preceding embodiment, said controller further comprising: (a) a computer processor; and (b) a non-transitory computer-readable memory storing instructions executable by the computer processor; (c) wherein said instructions, when executed by the computer processor, perform steps comprising: (i) controlling the X-Y position of the printing head assembly; (ii) controlling the Z position of the printing surface of the constant temperature liquid container; and (iii) controlling the fluid dispensed by the dispenser of the printing head assembly.

10. The apparatus of any preceding embodiment, wherein said instructions when executed by the computer processor further perform steps comprising: sensing a constant temperature liquid level in the constant temperature liquid container; and actuating the valve to allot a volume of constant temperature liquid to the constant temperature liquid container to maintain a set liquid level; wherein the constant temperature liquid level is maintained at a level that is approximately flush with the surface of the last printed layer.

11. The apparatus of any preceding embodiment, wherein said instructions when executed by the computer processor further perform steps comprising: providing a three-dimensional object design of cross-sectional slices to define the respective layers for construction by the apparatus; and dispensing fluid with the dispenser on the printing surface according to each cross-sectional slice of the object design.

12. The apparatus of any preceding embodiment, wherein said instructions when executed by the computer processor further perform steps comprising: sensing the temperature of the fluid in the printing head assembly; controlling the temperature of the fluid dispensed from the printing head assembly; controlling the cooling rate of the printed layer; and controlling the temperature of the constant temperature liquid in the constant temperature liquid container.

13. A method for cryogenic 3D printing of an object, the method comprising: (a) dispensing a fluid material onto a printing surface to form a layer of a 3D printed solid object, said material having a phase transition temperature, the printing surface having a temperature equal or lower than the phase transition temperature of the fluid material; (b) repeating step (a) to print multiple layers, wherein a previously printed layer serves as the printing surface for a subsequently printed layer; (c) immersing the entire printed object to the printed layer in an immersion liquid having a constant temperature that is lower or equal to the phase transition temperature of the printed material as each layer is printed; and (d) continuously raising the level of immersion liquid so that the liquid level is maintained at a level that is approximately flush with a top surface of the last printed layer.

14. The method of any preceding embodiment, further comprising: sensing a temperature of the fluid material prior to being dispensed; controlling the temperature of the dispensed fluid material; and controlling the volume of fluid material dispensed on a printing surface.

15. The method of any preceding embodiment, further comprising: controlling the cooling rate of the printed fluid material in each deposited layer.

16. The method of any preceding embodiment, further comprising: controlling the rate of deposition of fluid material in each deposited layer.

17. The method of any preceding embodiment, further comprising: sensing the temperature of the immersion liquid; and controlling the temperature of the immersion liquid.

18. The method of any preceding embodiment, further comprising: (a) dispensing a second fluid material onto a printing surface to form a layer of a 3D printed solid object, said second material having a phase transition temperature, the printing surface having a temperature equal or lower than the phase transition temperature of the second fluid material; (b) repeating step (a) to print multiple layers, wherein a previously printed layer serves as the printing surface for a subsequently printed layer; (c) immersing the entire printed object to the printed layer in an immersion liquid having a constant temperature that is lower or equal to the phase transition temperature of the printed material as each layer is printed; and (d) continuously raising the level of immersion liquid so that the liquid level is maintained at a level that is approximately flush with a top surface of the last printed layer.

19. The method of any preceding embodiment, further comprising: removing the complete printed object from the immersion liquid; placing the printed object in a vacuum chamber and evacuating the chamber; sublimating frozen fluids in the printed object; and desorption drying any remaining fluids bound to the printed object.

20. The method of any preceding embodiment, wherein said fluid material is a material selected from the group of materials consisting of collagen, alginate, fibroin and chitin.

21. The method of any preceding embodiment, wherein said fluid material comprises alginate and a cross-linking agent.

22. The apparatus of any of any preceding embodiment, wherein said apparatus is used in the construction of biological complex cell-containing scaffolds used in tissue engineering, including incorporation of multifunctional stem cells.

23. The apparatus of any preceding embodiment, wherein said apparatus is used in combination with a controlled drying process to construct stable scaffolds with and without cells applicable to tissue engineering systems.

24. The apparatus of any of any preceding embodiment, wherein said apparatus is used in the production of foods which retain nutritional quality, viability, and long-term stability.

25. The method of any of any preceding embodiment, wherein said method is used in the construction of biological complex cell-containing scaffolds used in tissue engineering, including incorporation of multifunctional stem cells.

26. The method of any preceding embodiment, wherein said method is used in combination with a controlled drying process to construct stable scaffolds with and without cells applicable to tissue engineering systems.

27. The method of any preceding embodiment, wherein said method is used in the production of foods which retain nutritional quality, viability, and long-term stability.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for cryogenic 3D printing of an object, the method comprising:
    (a) sensing a temperature of a fluid material of a mixture of water and at least one type organic molecule to be dispensed;
    (b) controlling the temperature of the fluid material to be dispensed;
    (c) dispensing the fluid material onto a printing surface to form a layer of a 3D printed solid object, said material having a phase transition temperature, the printing surface having a temperature equal or lower than the phase transition temperature of the dispensed fluid material;
    (d) repeating step (c) to print multiple layers, wherein a previously printed layer serves as the printing surface for a subsequently printed layer;
    (e) immersing the entire printed object to about the level of the last printed layer in an immersion liquid having a constant temperature that is lower or equal to the phase transition temperature of the printed material as each layer is printed;

(f) continuously adjusting the level of immersion liquid so that the liquid level is maintained at a level that is approximately flush with a top surface of the last printed layer;
(g) sensing the temperature of the immersion liquid;
(h) controlling the temperature of the immersion liquid; and
(i) sensing the distance between the level of the immersion fluid and a top surface of the last printed layer.

2. The method of claim 1, further comprising:
controlling the cooling rate of the printed fluid material in each deposited layer.

3. The method of claim 1, further comprising:
controlling the rate of deposition of fluid material in each deposited layer.

4. The method of claim 1, further comprising:
(a) dispensing a second fluid material onto a printing surface to form a layer of a 3D printed solid object, said second material having a phase transition temperature, the printing surface having a temperature equal or lower than the phase transition temperature of the second fluid material;
(b) repeating step (a) to print multiple layers, wherein a previously printed layer serves as the printing surface for a subsequently printed layer;
(c) immersing the entire printed object to the printed layer in an immersion liquid having a constant temperature that is lower or equal to the phase transition temperature of the printed material as each layer is printed; and
(d) continuously adjusting the level of immersion liquid so that the liquid level is maintained at a level that is approximately flush with a top surface of the last printed layer.

5. The method of claim 1, further comprising:
removing the complete printed object from the immersion liquid;
placing the printed object in a vacuum chamber and evacuating the chamber;
sublimating frozen fluids in the printed object; and
desorption drying any remaining fluids bound to the printed object.

6. The method of claim 1, wherein said fluid material is a mixture of water and an organic material selected from the group of materials consisting of collagen, alginate, fibroin and chitin.

7. The method of claim 1, wherein said fluid material comprises alginate.

* * * * *